United States Patent [19]

Ballato

[11] Patent Number: 4,598,224

[45] Date of Patent: Jul. 1, 1986

[54] SURFACE ACOUSTIC WAVE DEVICE FOR SENSING THE PRESENCE OF CHEMICAL AGENTS

[75] Inventor: Arthur Ballato, Long Branch, N.J.

[73] Assignee: The United States of America as represented by the Secretary of the Army, Washington, D.C.

[21] Appl. No.: 763,164

[22] Filed: Aug. 7, 1985

[51] Int. Cl.⁴ ............................................. H01L 41/08
[52] U.S. Cl. ............................... 310/313 R; 310/311; 310/313 D; 333/153; 73/23; 422/98
[58] Field of Search .............. 310/311, 313 R, 313 B, 310/313 C, 313 D, 312; 333/153, 195; 73/23, 24; 422/98; 435/4-10, 12, 14, 15, 25, 29

[56] References Cited

U.S. PATENT DOCUMENTS

| | | | |
|---|---|---|---|
| 4,210,722 | 7/1980 | Silver | 310/311 X |
| 4,246,344 | 1/1981 | Silver, III | 310/311 X |
| 4,312,228 | 1/1982 | Wohltjen | 310/313 R X |
| 4,343,688 | 8/1982 | Harwood | 310/313 R X |

FOREIGN PATENT DOCUMENTS 0100238  8/1979  Japan ............................. 310/313 D

OTHER PUBLICATIONS

Palladium-Surface Acoustic Wave Interaction for Hydrogen Detection by A. D'Amico et al., Applied Physics Letters, vol. 41, No. 3, Aug. 1982, pp. 300-301.

Primary Examiner—Mark O. Budd
Attorney, Agent, or Firm—Anthony T. Lane; Sheldon Kanars; Roy E. Gordon

[57] ABSTRACT

A surface acoustic wave device is provided for sensing the presence of chemical agents by chemo-electronic means. The device includes a quartz substrate and means deposited on the substrate for propagating and receiving surface acoustic waves along the surface of the substrate. Regions are provided on the substrate containing etched tunnels, the walls of the etched tunnel being coated within with a chemical substance sensitive to the chemical agent to be detected. When surface acoustic waves are caused to pass over these regions, the reaction of the chemical agent to be detected with the chemical substance causes a change in the acoustic wave velocity.

5 Claims, 4 Drawing Figures

SURFACE ACOUSTIC WAVE DEVICE FOR SENSING THE PRESENCE OF CHEMICAL AGENTS

The invention described herein may be manufactured, used, and licensed by or for the Government for governmental purposes without the payment to me of any royalty thereon.

This invention is an improvement of the invention disclosed and claimed in U.S. patent application Ser. No. 763,160 filed 8-7-85 by Arthur Ballato for "Improved Chemical Sensor Matrix" with which this application is copending and assigned to a common assignee.

BACKGROUND OF THE INVENTION

Ser. No. 763,160 discloses and claims a chemical sensor matrix that operates by chemo-electronic means, that has configuration adaptable for the detection of many chemical agents, that is small in size, of light weight, low in cost and that has a high sensitivity of detection. The chemical sensor matrix is comprised of a plurality of bulk acoustic wave (BAW) resonators embedded in a single monolithic piece of piezoelectric crystal. The resonators are arranged in rectangular row and column configuration including m rows and n columns, the (mn) th resonator having nominal frequency $f_{mn}$ and each of the resonators being separated from its neighboring resonators by distances such that the resonant energies do not overlap. Each of the resonators is provided with etched tunnels that are coated within by a chemical substance particular to that resonator and different from the chemical substance used to coat any other resonator, the chemical substance being sensitive to a chemical agent to be detected so that when the chemical agent reacts with the chemical substance the frequency $f_{mn}$ changes. Each of said rows of resonators bears a metallic electrode stripe for that row, and each of said columns of resonators bears a metallic electrode stripe for that column. The electrode row stripes are positioned on the top surface of the crystal, and the electrode column stripes are positioned on the bottom surface of the crystal. The areas of overlap of the row and column stripes are registered with the central portions of the embedded resonators. Two diode arrays are positioned on the periphery of the crystal for addressing the individual row electrode stripes and the individual column electrode stripes so that the desired resonator can be activated by connecting the stripe corresponding to its row address and the stripe corresponding to its column address to suitable active oscillator circuitry and signal processing means. The resonators (mn) are then interrogated sequentially and frequency changes registered.

In addition to the etched tunnels coated within by a chemical substance to be sensitive to a chemical agent to be detected, each of the resonators may also be coated on its surface with the chemical substance used to coat within the etched tunnel of that resonator. The two types of coatings acting together can enhance the sensitivity of the resonator to an even greater extent than either coating acting alone.

Although the BAW configuration as disclosed and claimed in Ser. No. 763,160 is adequate, it still lacks the capacity for microwave frequency application. To overcome this problem, one must provide a chemical sensor capable of higher frequency application compatible with modern communications technology and even more sensitive to the effects of mass loading and stress biases.

SUMMARY OF THE INVENTION

The general object of this invention is to provide a device or chemical sensor for sensing the presence of chemical agents. A further object of the invention is to provide such a chemical sensor that operates by chemo-electronic means. A still further object of the invention is to provide such a chemical sensor that will have a configuration adaptable for the detection of many chemical agents, that will be small in size, of light weight, and low in cost. Another object of the invention is to provide an improved chemical sensor that will have a high sensitivity of detection. Another object of the invention is to provide an improved chemical sensor capable of higher frequency application compatible with modern communications technology and even more sensitive to the effects of mass loading and stress biases.

It has now been found that the aforementioned objects can be attained using surface acoustic waves that propagate along the surface of the crystal or substrate. More particularly, according to the invention, a surface acoustic wave (SAW) device is provided for sensing the presence of chemical agents by chemo-electronic means. The device includes a quartz substrate and means deposited on the substrate for propagating and receiving surface acoustic waves along the surface of the substrate. Regions are provided on the substrate containing etched tunnels; the inner walls of the etched tunnels being coated with a chemical substance sensitive to the chemical agent to be detected. When surface acoustic waves are caused to pass over these regions, the reaction of the chemical agent to be detected with the chemical substance causes a change in the acoustic wave velocity.

The surface acoustic waves penetrate the substrate only to a depth of about 1 or 2 acoustic wavelengths as opposed to the bulk acoustic waves which travel within the volume of the crystal. The surface acoustic waves are generated according to the invention by an electrode array called an Interdigital Transducer (IDT). These electrode arrays are comprised of comb-like structures that are interdigital so that a voltage may be applied between the two different combs. When a voltage is applied to the IDT, surface acoustic waves are produced that propagate in both directions away from the array. IDT's may be used not only to create surface acoustic waves but also to detect surface acoustic waves in much the same way that an antenna in electromagnetics can be used to transmit or to receive electromagnetic waves. The IDT array is normally drawn as a rectangular box with an X placed in it. This simple schematic representation simplifies the drawing of these arrays. If a box with an X does not have lead wires attached, it is presumed that the interdigitated fingers act merely as reflectors of surface acoustic waves. If the box containing the X does have terminal wires attached, then it is presumed that the IDT either transduces surface acoustic waves or receives surface acoustic waves. The present invention encompasses producing surface acoustic waves, receiving surface acoustic waves and reflecting surface acoustic waves.

DESCRIPTION OF THE DRAWING

Referring to FIG. 1, and FIG. 2, the SAW delay line includes a quartz substrate, 10 upon which is deposited an input IDT, 12 at one end and an output IDT, 14 at the other end. The input IDT, 12 produces the surface acoustic wave, 16 that propagates along the quartz substrate, 10 and is received at some later time by the output IDT, 14. During its journey from input IDT, 12 to output IDT, 14 the surface acoustic wave, 16 traverses a path on the substrate, 10 containing a region that has etched tunnels, 18 produced in it. These etched tunnels, 18 have their inner walls coated with a chemical substance that is sensitive to the chemical agent desired to be detected. If the chemical agent is not present, then the surface acoustic wave, 16, propagating from input IDT, 12 to output IDT, 14 passes over the region with the etched tunnels, 18 but does not interact strongly and is received at the output IDT, 14. The delay time from input IDT, 12 to output IDT, 14 is a certain number that is calibrated. On the other hand, should the chemical agent to be detected be present, its strong chemical reaction with a chemical substance in the etched tunnels 18 produces mechanical stresses in the substrate, 10. These mechanical stresses distort the substrate, 10 and change the acoustic wave velocity of the surface acoustic wave, 16. Therefore, the time of flight of the surface acoustic wave, 16 from input IDT, 12 to output IDT, 14 is changed. Because the time of flight is changed, when the delay line is built into an oscillator, its frequency will be shifted from that that obtains when the surface acoustic wave is not perturbed. Therefore, the chemical agent in producing a shift in frequency is detected.

Referring to FIG. 3, another type of SAW device different from the delay line variety is the so-called SAW resonator. The SAW resonator is more strictly analogous to a bulk wave resonator in that the waves are produced, then they are reflected from end faces and are turned back into the generating structure to produce a resonance. FIG. 3 shows such a SAW resonator. FIG. 3 is described as a one-port resonator meaning that in its very center it has deposited on the top of quartz substrate 10, a central array IDT 20, with terminal wires or lead wires. This central array 20 produces surface acoustic waves that propagate both to the left and the right away from this transmitter. Both the leftgoing and the rightgoing surface acoustic waves pass over regions containing etched tunnels, 18. After passing this region, they approach IDT's, one IDT, 22 on the extreme left and another IDT 22' on the extreme right. These IDT's are not provided with lead wire terminals. These IDT's are merely surface acoustic wave reflectors. Each finger of the reflecting IDT's, 22 and 22' respectively, reflects a very small amount, less than one percent, perhaps a tenth of a percent or a hundreth of a percent of the incident surface wave energy. However, the cumulative effect of all of the fingers in the reflecting IDT is such as to produce nearly total reflection of the incident SAW energy. The operation of these reflectors is similar to the reflection that takes place in a crystal with regard to X-rays. Each crystal plane reflects a very small amount of the incident X-rays but the cumulative effect over many layers of atoms is such as to produce nearly total reflection of the incident SAW energy. Thus, these reflecting IDT's might be referred to as distributed mirrors. The surface waves then produced by the central IDT 20 are launched to the left and to the right, pass over the sensitive region, are reflected by the distributed arrays at the end, 22 and 22' respectively, and are turned back towards the central generating and receiving array, 20. They thus make a double pass over the sensitive region. When they arrive back at the central array, 20, they form standing acoustic waves at the frequency of resonance. When the central IDT, 20 is connected to oscillator circuitry, it will come to a certain resonance frequency in the same manner as the delay line of FIG. 1. However, if in passing over the etched tunnels, 18 to the left and to the right of the central array, 20, the surface acoustic waves encounter regions of stress produced by the interaction of the chemical agent to be detected with the chemical substance in the etch tunnels, 18, then in the same manner as in FIG. 1, the velocity of the acoustic waves will be altered. Consequently, the SAW one-port resonator frequency will likewise be altered.

Referring to FIG. 4, this is yet another embodiment of the SAW device. This is a SAW two-port resonator. It is comprised of two interdigital transducers, each with terminal wires, one being an input IDT, 12 and the one next to it being the output IDT, 14. The reason for the two IDT's rather than one as in FIG. 3 is that the static capacitance between the input and output IDT's is much less, and it is much more suitable for oscillator operation. The remaining operation of the two-port resonator is very similar to that of FIG. 3 which is the one-port resonator. That is, the acoustic waves are transduced by the input IDT, 12, and they propagate in both directions to the left and to the right. When the waves reach the far ends of the device, they encounter the IDT reflectors 22 and 22' respectively. The waves are reflected from those reflectors and pass back through to the output IDT, 14. During their flight from the input IDT, 12 to the output IDT, 14 and during their reflection from the IDT reflectors, 22 and 22' respectively, they make two passes over the sensitive region containing the etched tunnels, 18 where, if the chemical agent to be detected produces high stresses in the quartz, the velocity of the surface acoustic wave is perturbed. This in turn affects the frequency of the oscillator to which the device is connected.

Figure 1:
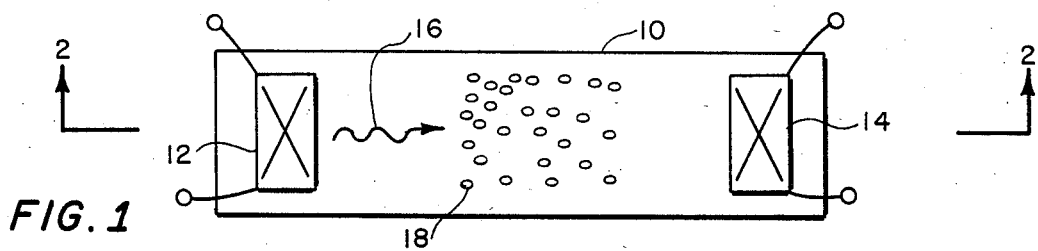
FIG. 1 shows a plan view of a SAW delay line according to the invention in which an input IDT array produces the surface acoustic wave that propagates along a quartz or other piezoelectric material substrate and is received at some later time by the output IDT.
Figure 2:
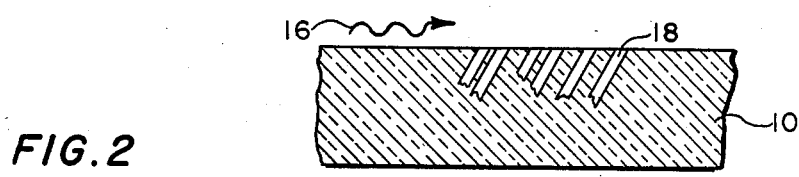
FIG. 2 represents a cross sectional view taken along the length axis of FIG. 1 showing on the top schematically how the surface acoustic wave propagates from input to output passing over the region with the etched tunnels.
Figure 3:
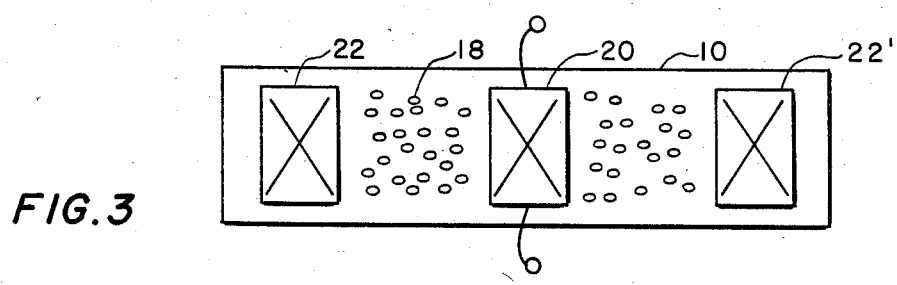
FIG. 3 shows a plan view of a SAW one-port resonator in which waves are produced and reflected from end faces and turned back into the generating structure to produce a resonance.
Figure 4:
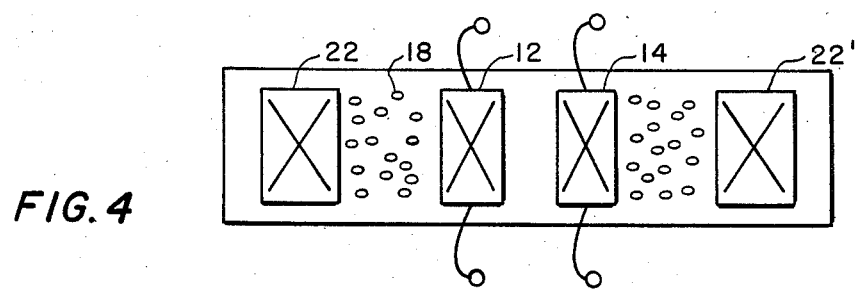
FIG. 4 shows a plan view of a SAW two-port resonator including two interdigital transducers, each with terminal wires, one being an input IDT and the one next to it being the output IDT.

In the invention, the etched tunnels in the sensitive region may be formed by photolytic etching, by laser-assisted wet etching, etc. The concentration of etched tunnels in the sensitive region depends on etchant means and durations, as well as quality of quartz, i.e., distribution and concentration of impurities and dislocations.

If more than one chemical agent is to be detected, then multiple surface acoustic wave devices for the detection of many chemicals agents can be obtained by utilizing the concept of a matrix array as disclosed in Ser. No. 763,160 with the replacement of the bulk acoustic wave (BAW) elements used therein by surface acoustic wave (SAW) elements of the type disclosed herein. Each SAW element of the matrix array would be provided with its own chemical means for detecting a specific chemical agent.

I wish it to be understood that I do not desire to be limited to the exact details as described for obvious modifications will occur to a person skilled in the art.

What is claimed is:

1. A surface acoustic wave device for sensing the presence of chemical agents by chemo-electronic means, said device comprising a quartz substrate, means deposited on the substrate for propagating and receiving surface acoustic waves along the surface of the quartz substrate and regions on said substrate containing etched tunnels coated within the walls of the tunnel with a chemical substance sensitive to the chemical agent to be detected so that when surface acoustic waves are caused to pass over these regions, the reaction of the chemical agent to be detected with the chemical substance causes a change in the acoustic wave velocity.

2. A surface acoustic wave device according to claim 1 wherein said means for propagating and receiving surface acoustic waves are interdigital transducer electrode arrays.

3. A surface acoustic wave device according to claim 2 including an input interdigital transducer electrode array with terminal wires for propagating surface acoustic waves deposited on top of the quartz substrate at one end of the substrate, an output interdigital transducer electrode array with terminal wires, for receiving surface acoustic waves deposited on top of the quartz substrate at the other end of the substrate with said region containing etched tunnels coated within the walls of the tunnel with a chemical substance sensitive to the chemical agent to be detected located between said input interdigital transducer electrode array and said output interdigital transducer electrode array.

4. A surface acoustic wave device according to claim 2 including an interdigital transducer electrode array with terminal wires deposited on top of the quartz substrate in the center of the substrate, an interdigital transducer electrode array deposited on the top of the quartz substrate at one end of the quartz substrate, and another interdigital transducer electrode array deposited on the top of the quartz substrate at the other end of the substrate, the two said interdigital transducer electrode arrays at the ends of the quartz substrate serving as surface acoustic wave reflectors, with a region containing etched tunnels coated within the walls of the tunnel with a chemical substance sensitive to the chemical agent to be detected located between one of the end electrode arrays and the centrally positioned electrode array and a second region containing etched tunnels coated within the walls of the tunnel with a chemical substance sensitive to the chemical agent to be detected located between the other end electrode array and the centrally positioned electrode array.

5. A surface acoustic wave device according to claim 2 including an input interdigital transducer electrode array with terminal wires for propagating surface acoustic waves deposited on the top of the quartz substrate near the center of the substrate, an output interdigital transducer electrode array with terminal wires for receiving surface acoustic waves deposited on the top of the quartz substrate near the center of the substrate, adjacent to but spaced from said input interdigital transducer electrode array, an interdigital transducer electrode array deposited on the top of the quartz substrate at one end of the quartz substrate, and another interdigital transducer electrode array deposited on the top of the quartz substrate at the other end of the substrate, the two said interdigital transducer electrode arrays at the ends of the quartz substrate serving as acoustic wave reflectors, with a region containing etched tunnels coated within the walls of the tunnel with a chemical substance sensitive to the chemical agent to be detected located between one of the end electrode arrays and the input interdigital transducer electrode array and a second region containing etched tunnels coated within the walls of the tunnel with a chemical substance sensitive to the chemical agent to be detected located between the other end electrode array and the output interdigital transducer electrode array.

* * * * *